United States Patent [19]
Famulok et al.

[11] Patent Number: 5,834,198
[45] Date of Patent: Nov. 10, 1998

[54] SELECTIVE PHOTOINDUCTED FLAVIN-DEPENDENT CLEAVAGE OF RNA AT G-U BASE PAIRS AND KITS THEREFOR

[75] Inventors: Michael Famulok; Petra Burgstaller, both of Munich, Germany

[73] Assignee: Boehringer Mamnnheim GmbH, Mannheim, Germany

[21] Appl. No.: 769,004

[22] Filed: Dec. 18, 1996

Related U.S. Application Data

[60] Provisional application No. 60/013,823 Mar. 21, 1996.
[51] Int. Cl.⁶ .............................. C12Q 1/68; C07H 19/00
[52] U.S. Cl. .................................................. 435/6; 536/22.1
[58] Field of Search ................................. 435/6; 536/22.1

[56] References Cited

U.S. PATENT DOCUMENTS 4,604,356  8/1986  Blake, II .................................. 435/194

OTHER PUBLICATIONS

Stratagene Catalog, p. 39, 1988.
Sigma Chemical Company "Biochemicals organic compounds for research and diagnostic reagents", p. 2012 1992.

Primary Examiner—Ardin H. Marschel
Assistant Examiner—Jezia Riley
Attorney, Agent, or Firm—Nikaido Marmelstein Murray & Oram LLP

[57] ABSTRACT

Disclosed is a method of cleaving an RNA molecule containing at least one G-U wobble base pair at the at least one G-U wobble base pair thereof. Also disclosed are kits for use in such a method

17 Claims, 13 Drawing Sheets

FMN/FAD binding site

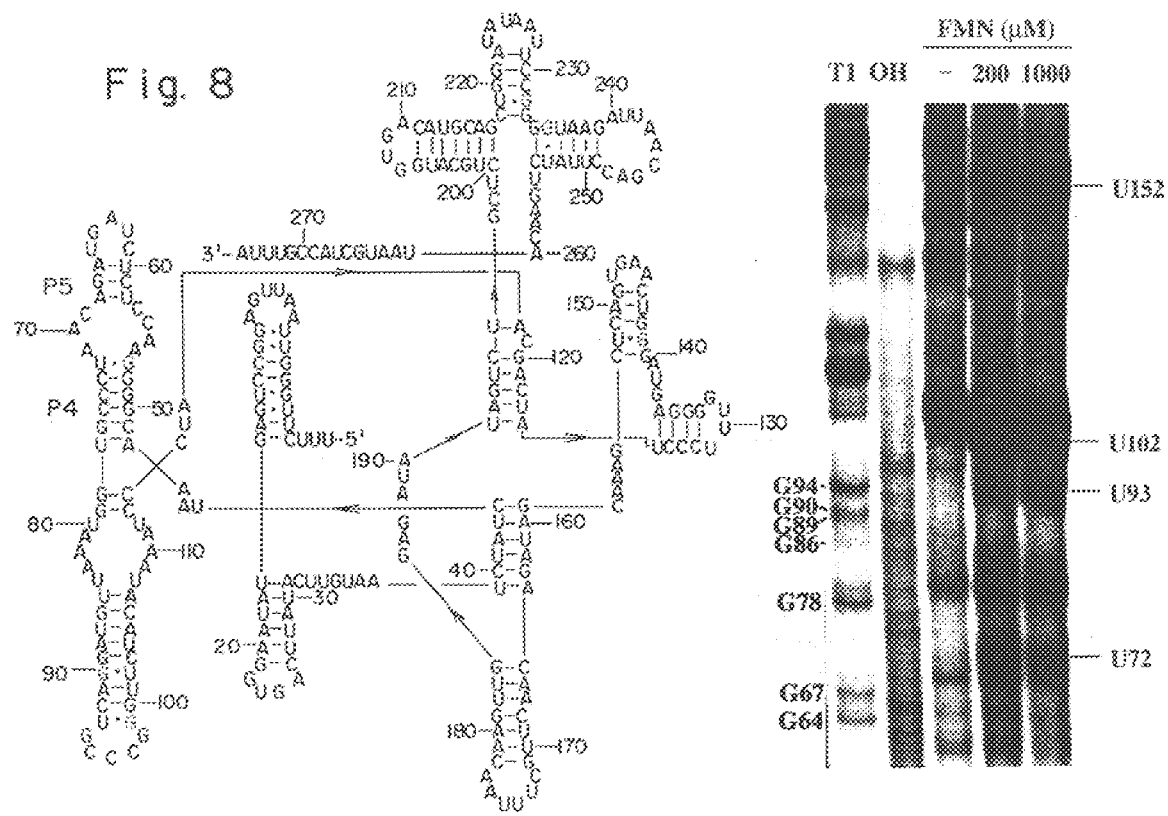

SELECTIVE PHOTOINDUCTED FLAVIN-DEPENDENT CLEAVAGE OF RNA AT G-U BASE PAIRS AND KITS THEREFOR

This application, claims the benefit of U.S. Provisional Application No. 60/013,823, filed Mar. 21, 1996, abandoned.

BACKGROUND OF THE INVENTION

Certain kinds of light-activated compounds termed photosensitizers are able to damage cells and organisms due to their effect on critical biomolecules. Some of these photosensitizers such as porphyrins and flavins are endogenous and are thought to play a role in photocarcinogenesis because the products formed may cause misreplication of DNA and therefore might lead to mutations and cancer. It is also known that some exogenous photosensitizers like polycyclic aromatic hydrocarbons are able to induce tumor generation upon irradiation. Natural and synthetic photosensitizers have attracted considerable interest because of their utilization in photochemotherapy, the treatment of diseases with photosensitizing drugs plus light. The most successful example of this technique is the treatment of psoriasis with a combination of orally applied psoralens and artificial ultraviolet A radiation. Morison, W. L. (1983) *Phototherapy and Photochemotherapy of skin diseases.* Praeger, Westport. Another important application of photochemotherapy is the treatment of tumors with photosensitizers like hematophorphyrin. Diamond, I. et al. (1972) *Lancet* 2, 1175.

Mechanisms of photosensation can be divided into two classes; in type I mechanisms, the photosensitizer directly interacts with the target molecule by either abstraction or donation of electrons or H-atoms. During this process, free radicals are generated both in the sensitizer and substrate molecules. In many cases, the resulting substrate radicals react with oxygen to give oxidized products of various types. In type II mechanisms, the excited photosensitizer interacts with ground state oxygen to generate a singlet oxygen molecule, $^1O_2$, which can readily react with electron-rich regions of many biomolecules to yield oxidized species. Spikes, J. D. (1989) Photosensation, in *The science of photobiology.* (Smith, K. C., ed.) 2nd Edition, Plenum Press, New York, pp. 79–111.

Flavin derivatives like flavin mononucleotide (FMN) were found to induce DNA damage in a photooxidative mechanism by generating 8-hydroxy-deoxyguanosine. Naseem, I. et al. (1988) *Biosci. Rep.* 8, 485–492. Kasai, H. et al. (1992) *J. Am. Chem. Soc.* 114, 9692–94. Buchko, G. W. et al. (1992) *Nucl. Acids Res.* 20, 4847–51. Ito, K. et al. (1993) *J. Biol. Chem.* 268, 13221–27. An artificial restriction endonuclease activity was obtained by a synthetic netropsin-flavin hybrid molecule which cleaves DNA at a specific A:T-rich locus determined by the sequence specificity of the netropsin moiety. Bouziane, M. et al. (1995) *Biochem.* 34, 14051–58.

Treatment of dsDNA with photosensitizers, including flavins, were found to affect mainly the guanine residues. In most cases, cleavage was observed only after incubation with piperidine (Ito, K. et al. (1993) *J. Biol. Chem.* 268, 13221–27) and mechanisms in which the photosensitizer directly or indirectly destroyed the base have been suggested (Buchko, G. W. et al. (1992) *Nucl. Acids Res.* 20, 4847–51). A non-endogenic system consisting of a isoalloxazine ring covalently attached to either netropsin (Bouziane, M. et al. (1995) *Biochem.* 34, 14051–58) or distamycin (Herfeld, P. et al. (1994) *Bioconjug. Chem.* 5, 67–76) was synthesized and resulted in a single strand break in dsDNA upon irradiation with visible light. In this cleavage mechanism, an attack at the deoxyribose induced by the irradiated isoalloxazine moiety was discussed. Sequence specificity for A:T-rich regions was observed which resulted from the attached groove binders, however.

In contrast to the well demonstrated effect on DNA, little is known about the effect of photosensitizers on RNA. Particularly, it is unknown whether RNA is a target for the photoinduced cleavage by flavins or flavin derivatives. The only known example showing that RNAs are affected by photosensitizers is the psoralen induced photocrosslinking (Cimino, G. D. et al. (1985) *Annu. Rev. Biochem.* 54, 1151–93) of various positions in ribosomal RNAs, tRNAs and the spliceosome. The major psoralen-reactive base in RNA is uridine (Thompson, J. F. et al. (1981) *J. Mol. Biol.* 147, 417–36) but reaction with cytosine residues in tRNA has also been reported. Garrett-Wheeler, E. et al. (1984) *Nucl. Acids Res.* 12, 3405–23. The photoreaction of psoralens with RNA, however, occurs via a completely different mechanism than the cleavage mechanism described here.

The present inventors have now discovered the site specific cleavage of RNA by flavin derivatives such as FMN, riboflavin and lumiflavin via a photoinduced mechanism. Recently, the present inventors isolated RNA aptamers by SELEX (Gold, L. et al. (1995) *Annu. Rev. Biochem.* 64, 763–97) that specifically recognize the isoalloxazine moiety of FMN in solution. Burgstaller, P. et al. (1994) *Angew. Chem. Int. Ed. Engl.* 33, 1084–87. During the structural characterization of one of these aptamers (FMN-2), the present inventors discovered that flavin derivatives induce a strand breakage 3' of the uracil of G-U wobble base pairs in an oxidative cleavage reaction activated by light.

SUMMARY OF THE INVENTION

The subject of the present invention is, therefore, a method of cleaving an RNA molecule containing at least one G-U wobble base pair at the at least one G-U wobble base pair thereof by combining the RNA molecule with a photosensitizing flavin derivative which is capable of performing a photooxidative reaction with the RNA molecule upon irradiation with light and a divalent metal cation, or divalent metal salt, and thereafter cleaving the RNA molecule at the at least one G-U wobble base pair thereof by irradiating the mixture with light.

Further subject matter of the present invention is a method of cleaving an RNA molecule containing at least one G-U wobble base pair at the at least one G-U wobble base pair thereof by combining the RNA molecule with a photosensitizing flavin derivative which is capable of performing a photooxidative reaction with the RNA molecule upon irradiation with light and a divalent metal cation, or divalent metal salt, irradiating the mixture with light to cleave the RNA molecule at the G-U wobble base pair thereof, to produce at least one cleavage product, and then detecting the at least one cleavage product.

Still further subject matter of the present invention is a kit for cleaving an RNA molecule at at least one G-U wobble base pair thereof, including a photosensitizing flavin derivative which is capable of performing a photooxidative reaction with the RNA molecule upon irradiation with light and a divalent metal cation, or divalent metal salt.

BRIEF DESCRIPTION OF THE DRAWINGS

FIG. 1(*b*) shows the secondary structure of the flavin binding RNA aptamer FMN-2. The flavin binding site is highlighted.

FIG. 2(a–c) shows the photoinduced cleavage of the flavin binding RNA aptamer FMN-2 by FMN.

FIG. 3(a–b) shows the analysis of the end groups generated during the flavin-induced strand breakage reaction.

FIG. 6(a–b) shows the photoactivated cleavage of 5'-$^{32}$P-endlabeled RNA FMN-2.del with FMN. The cleavage site is indicated by the arrow. FIG. 6(a) shows the secondary structure of RNA FMN-2.del., while

FIG. 7(a–c) shows the photoinduced cleavage of $tRNA^{Phe}$, $tRNA^{Asp}$ and $tRNA^{fMet}$ from yeast with FMN. The cleavage sites are indicated by the arrow.

FIG. 8 shows the secondary structure of the td intron and analysis of the photoinduced FMN cleavage and shows the photoinduced cleavage of intron (delta P6-2) from a truncated version of the T4 phage derived td gene.

DESCRIPTION OF THE PREFERRED EMBODIMENTS

Figure 1A:
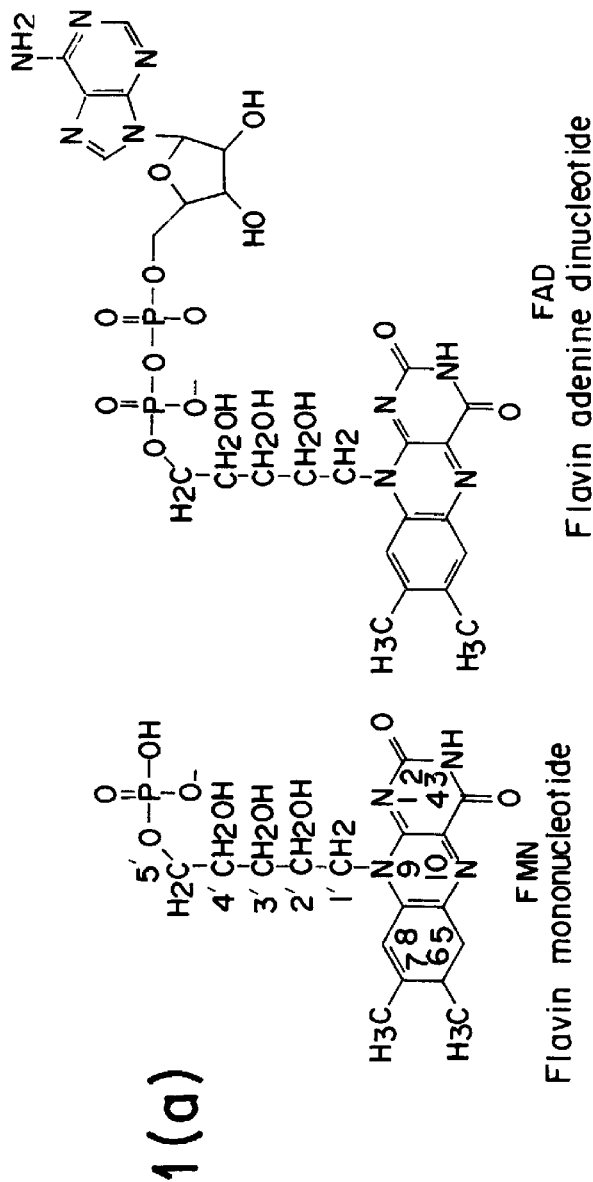
FIG. 1(*a*) shows the chemical structures of the derivatives used for photoinduced cleavage of RNA.
Figure 1A:
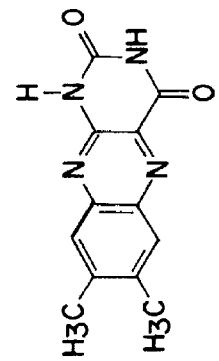
Figure 1A:
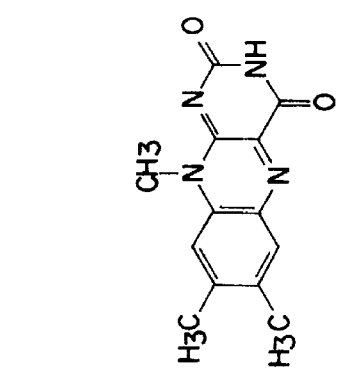
Figure 1A:
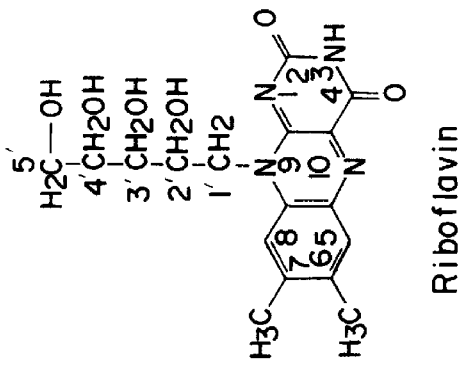

The present inventors have examined the effect of several flavin derivatives on a series of RNA molecules, including biologically relevant RNAs with known secondary and tertiary structures. It was found that flavin derivatives such as flavin mononucleotide (FMN), riboflavin, and lumiflavin lead to RNA cleavage, exclusively at G-U wobble base pairs within RNA helices, by removing one nucleotide downstream of the uracil residue upon irradiation with light. The effect depends on the presence of divalent metal ions but does not require monovalent metal ions. Biologically relevant RNAs such as $tRNA^{Phe}$, $tRNA^{Asp}$ and $tRNA^{fMet}$ from yeast as well as a group I intron RNA were also shown to be specifically cleaved at G-U base pairs.

Subject matter of the present invention is, therefore, a method of cleaving an RNA molecule containing at least one G-U wobble base pair at the at least one G-U wobble base pair thereof by combining the RNA molecule with a photosensitizing flavin derivative which is capable of performing a photooxidative reaction with the RNA molecule upon irradiation with light and a divalent metal cation, or divalent metal salt, and thereafter cleaving the RNA molecule at the at least one G-U wobble base pair thereof by irradiating the mixture with light.

Further subject matter of the present invention is a method of cleaving an RNA molecule containing at least one G-U wobble base pair at the at least one G-U wobble base pair thereof by combining the RNA molecule with a photosensitizing flavin derivative which is capable of performing a photooxidative reaction with the RNA molecule upon irradiation with light and a divalent metal cation, or divalent metal salt, irradiating the mixture with light to cleave the RNA molecule at the G-U wobble base pair thereof, to produce at least one cleavage product, and then detecting the at least one cleavage product.

Still further subject matter of the present invention is a kit for cleaving an RNA molecule at at least one G-U wobble base pair thereof, including a photosensitizing flavin derivative which is capable of performing a photooxidative reaction with the RNA molecule upon irradiation with light and a divalent metal cation, or divalent metal salt.

As the light source, visible light is preferred. However, other light sources, e.g. ultraviolet (UV) light, also are within the scope of the present invention.

The minimum exposure time for the irradiation procedure with a normal-intensity light source, e.g., an incandescent light source or a polychromatic lamp, can be, in some cases, less than 45 minutes (e.g., 15 to 45 minutes). Preferred exposure time is in a range of 45 to 60 minutes, but exposure can be for four hours or more, if desired. Exposure time can be shortened with the use of a high-intensity light source. An additional advantage of a high-intensity light source is that higher concentrations of a flavin derivative could be used to achieve a significant increase in effectivity. The effectivity of a normal-intensity light source is limited by the light absorption of the flavin structure above 200 μM.

The final concentration of divalent metal cation, or divalent metal salt, could be in a range of 2 to 50 mM. The range of 5 to 20 mM is preferred, and 10 to 15 mM is most preferred.

The concentration of flavin derivative to be used in accordance with the present invention can be in a range of 20 to 300 μM. Preferred is the range of 100 to 250 μM, and most preferred is 100 to 200 μM.

Figure 1B:
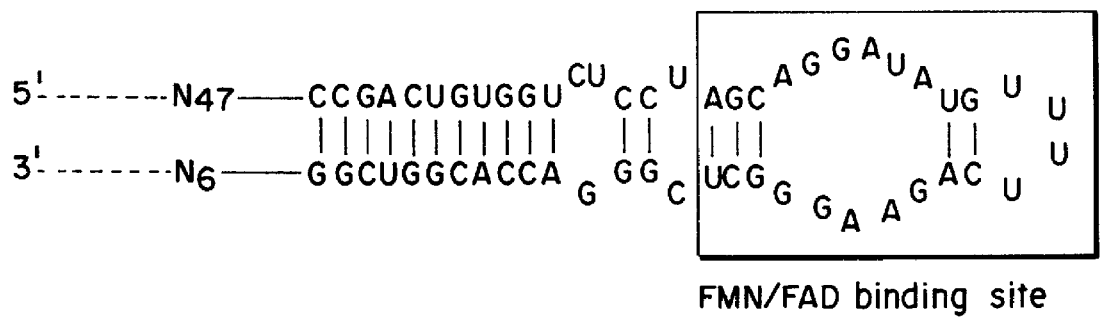

Referring to FIG. 1, the structure of FMN, FAD, riboflavin, lumiflavin and lumichrome are shown (FIG. 1(a)), along with the FMN/FAD binding site in an RNA aptamer (FIG. 1(b)). Flavin derivatives FMN, riboflavin and lumiflavin induce a strand breakage 3' of the uracil of G-U wobble base pairs in an oxidative cleavage reaction activated by light. This specific strand breakage appears to be a general mechanism which does not require an FMN or isoalloxazine binding site in the RNA. The present inventors have discovered that biologically relevant RNAs without any known affinity to flavins, such as $tRNA^{Phe}$, $tRNA^{Asp}$, $tRNA^{fMet}$, or the intron of a truncated version of the T4 phage td gene are specifically cleaved at G-U base pairs.

Photosensitizer flavin derivatives lead to specific strand breakage in ribonucleic acid. The photoinduced flavin-dependent cleavage of RNA is a general mechanism and occurs unexpectedly specific downstream of the U in G-U base pairs. The cleavage is initiated by an attack at the nucleotide located 3' of the uracil in the G-U pair. The attack results in the loss of this residue as concluded from the comparison of the termini of the 3'- and 5'-labeled RNAs obtained in the cleavage reaction with the sequencing ladder. This observation is further supported by the generation of 5'- and 3'-phosphate groups at the cleaved ends as deducted from FIG. 3, and the weaker cleavage signal in the tRNA$^{Asp}$ shown in FIG. 7(c). The fact that a nucleotide is attacked and removed is strongly indicative for an oxidative cleavage mechanism. This is also supported by the lack of cleavage obtained with lumichrome, an alloxazine derivative which cannot perform photooxidative reactions because of its conjugated ring system.

No bias exists with respect to the removed residue. Any nucleotide 3' of the G-U base pair at the cleavage site can be attacked and removed. This finding significantly differs from the sequence specificity observed in photosensitized cleavage of DNA and might indicate that it is the ribose moiety rather than the base which is attacked during the cleavage.

Figure 4:
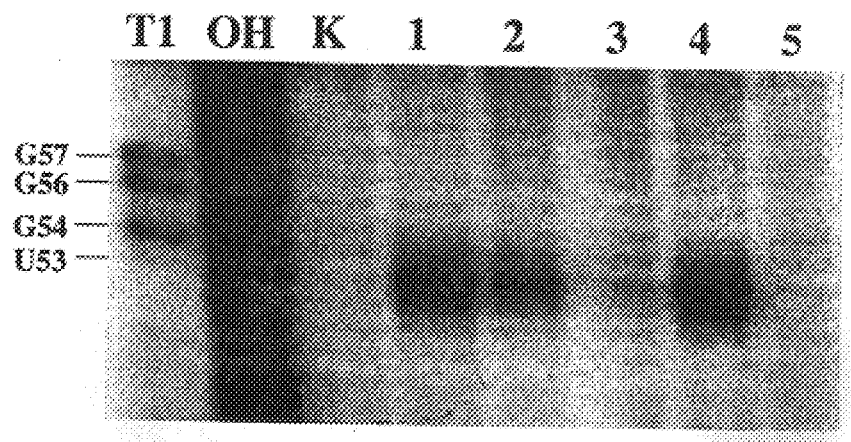
FIG. 4 shows the photoinduced cleavage of 5'-$^{32}$P-endlabeled RNA FMN-2 mediated by various isoalloxazine and alloxazine derivatives.

In the case of the RNA cleavage described here, strand breakage occurs in a highly specific manner at G-U wobble base pairs. Therefore, the present cleavage mechanism represents an example in which the cleavage site is determined by secondary structure and not the primary sequence. Several lines of evidence suggest that the isoalloxazine moiety specifically recognizes structural features within helical regions resulting from the presence of G-U base pairs. The molecular recognition process might involve intercalation of the flavin ring into the RNA helix. Strong evidence for this proposal results from inhibition studies performed with the non-photosensitizing isoalloxazine derivative FAD. FAD showed the expected lack of activity in the cleavage reaction (see FIG. 4).

It was also found that the specific strand scission requires the presence of divalent metal ions. In the presence of the alkaline earth metal ions $Mg^{2+}$, $Ca^{2+}$, $Sr^{2+}$, and $Ba^{2+}$ and also $Zn^{2+}$ and $Cd^{2+}$ the reaction is able to proceed equally well, whereas $Mn^{2+}$, $Cu^{2+}$, and $Pb^{2+}$ are unable to mediate cleavage. All these reactions contained 250 mM $Na^+$, but the cleavage still proceeds well when $Na^+$ is omitted from the cleavage buffer.

Figure 7A:
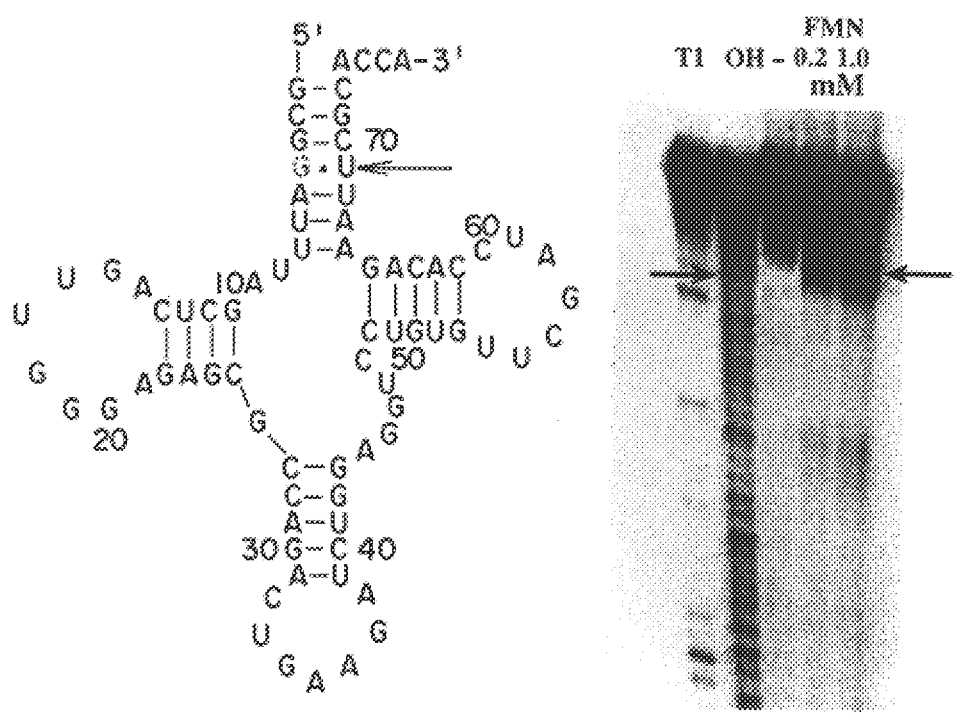
FIG. 7(a) shows the secondary structure of yeast $tRNA^{Phe}$ and analysis of the photoinduced FMN cleavage.
Figure 7B:
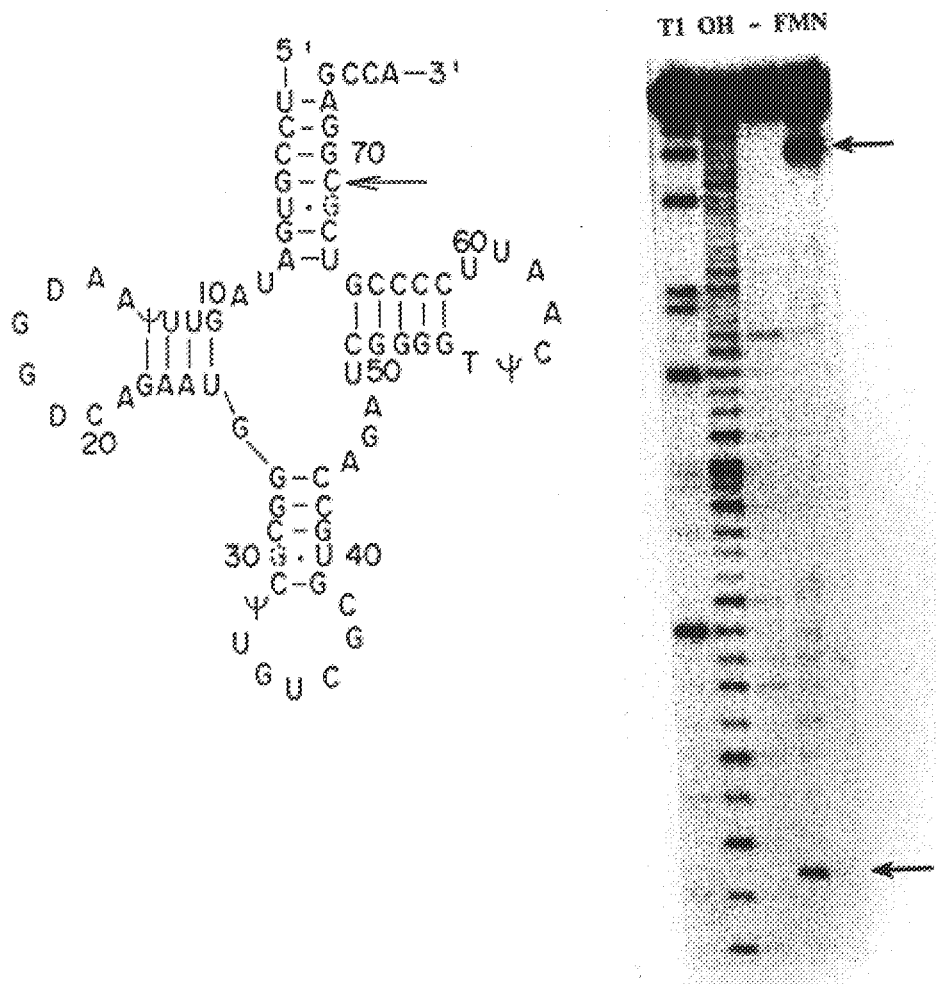
FIG. 7(b) shows the secondary structure of yeast $tRNA^{Asp}$ and analysis of the photoinduced FMN cleavage.
Figure 7C:
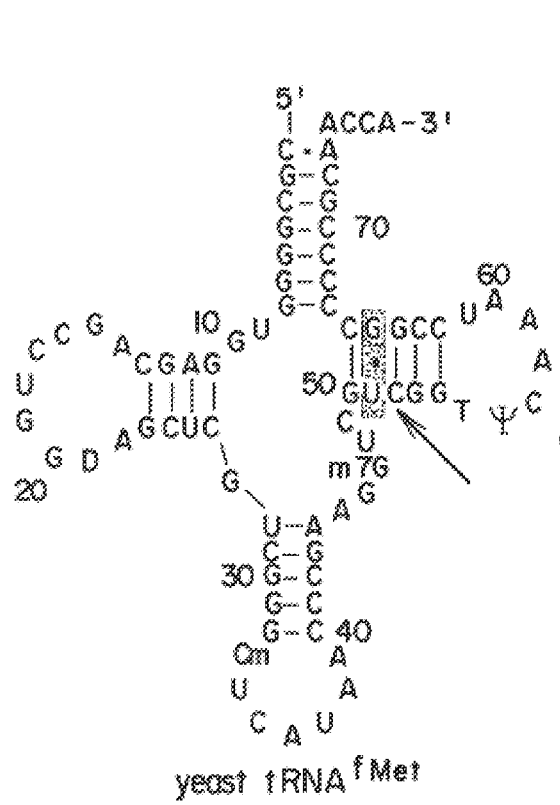
FIG. 7(c) shows the secondary structure of yeast $tRNA^{fMet}$ and analysis of the photoinduced FMN cleavage.
Figure 7C:
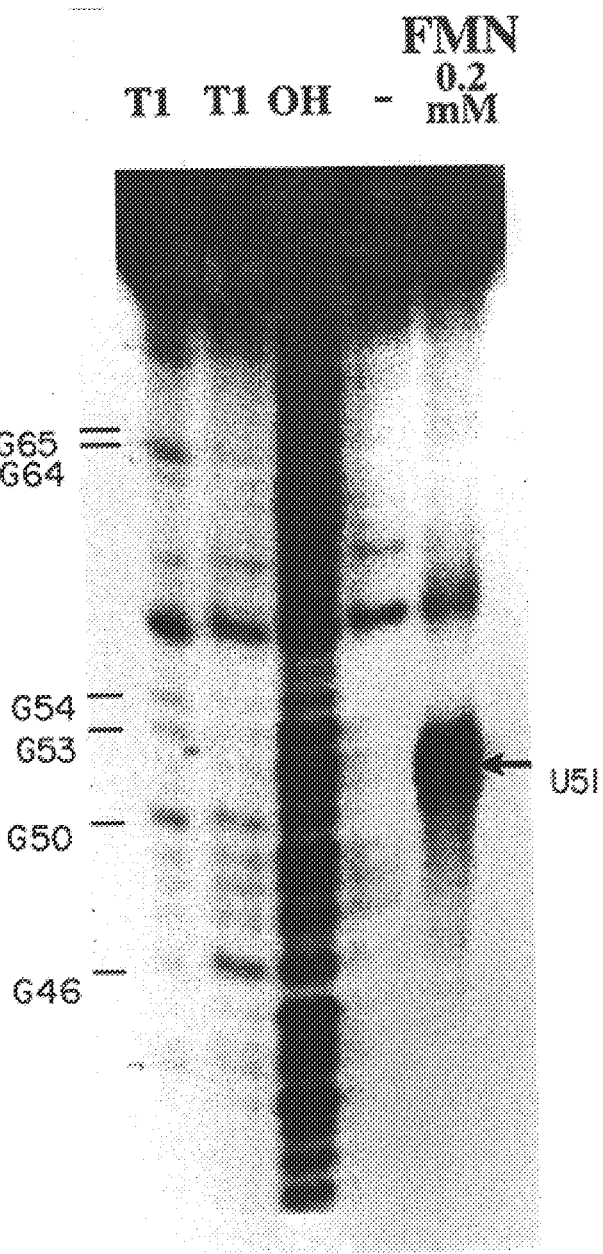

The generality of the cleavage mechanism and the remarkable specificity for G-U wobble pairs was further proven by examining biologically relevant RNA molecules with known secondary and/or tertiary structures. tRNA$^{Phe}$ and tRNA$^{Asp}$ from yeast and an intron of a truncated version of the T4 phage td gene were used as model systems. In all RNAs cleavage again was obtained exclusively at G-U base pairs. As shown in FIG. 7(a), at the single G-U pair present in the tRNA$^{Phe}$ cleavage is obtained while no other position in this RNA is affected by the photosensitizer. In contrast to tRNA$^{Phe}$, the tRNA$^{Asp}$ contains three G-U base pairs formed by G68-U5, G10-U25, and G30-U40, as well as a G22-Ψ13 base pair. FIG. 7(b) shows that cleavage is obtained only at G68-U5 and G30-U40 whereas no strand breakage occurred at G10-U25 and the G22Ψ13 base pair. FIG. 7(c) shows a cleavage bond at the single G-U base pair in tRNA$^{fMet}$ from yeast. In the td intron we also observed different degrees of cleavage at certain G-U pairs: while strong cleavage occurred at G90-U102 in stem P6a as well as at G141-U152 in P7.2 and G235-U253 in stem P9.2, weak cleavage was obtained at G53-U72 in stem P4 and G99-U93 in stem P6a. No strand break was detected in stem P1 at the 5'-splice site which contains two sets of two consecutive G-U pairs. The most likely explanation for the differences in the degree of cleavage might be the relative orientation of the attacked nucleotide with respect to the G-U base pair. As deduced from the structural data in the biologically relevant RNAs examined, all the uncleaved bases 3' of the uracils share in common that these residues are tilted out of the regular A-type helical geometry. This might result in an unfavorable conformation of the residue for the attack by the bound photosensitizer. It is likely that the isoalloxazine enters its G-U determined cleavage site from the shallow groove of the RNA. The 3'-end of the U is naturally accessible and points into the deep groove of the RNA. In case of the two sets of two consecutive base pairs in P1 of the td intron, the lack of cleavage activity might be explained by a change in the helix geometry caused by two aligned G-U pairs which can no longer be recognized by FMN.

It is clear that the isoalloxazine ring finds its cleavage site in a molecular recognition event governed by the G-U base pairs. As it is well established that RNA structures contain many different non-canonical base pairs, many of which are proven to be present also in the RNAs we used in the present invention, the specificity of the cleavage site selection by the photosensitizer isoalloxazine for an individual class of non canonical base pairs not only is remarkable, but also opens a potential application as a structure probe. For the first time it is possible to highly selectively probe an RNA structure for a non canonical base pair. Highly conserved G-U base pairs have been found to be present in many natural RNAs such as group I- and group II ribozymes, the spliceosome, and 16S and 23S ribosomal RNAs, and often were found to be functionally important.

The following examples further elucidate the invention.

EXAMPLES

Materials

Riboflavin, FMN, FAD, lumiflavin and lumichrome were purchased from Fluka, [γ-$^{32}$P]-ATP and [5'$^{32}$P]-pCp from Amersham. tRNA$^{Phe}$ was obtained from Sigma. NdC, a truncated version of the T4 phage derived td gene containing 79 nt of exon I, 265 nt of the intron (delta P6-2) and 21 nt of exon II cloned in the vector pTZ18U was a generous gift from Dr. R. Schroeder, University of Vienna (Streicher, B. et al. (1993) *Nucl. Acids Res.* 21, 311–17). T7 RNA polymerase was purified from the overproducing strain BL21/pAR1219, following the purification protocol provided by F. W. Studier (Davanloo, P. et al. (1984) *Proc. Natl. Acad. Sci. USA* 81, 2035–39), DNase I (RNase free) was from Boehringer Mannheim, Taq Polymerase from Eurogentec and T4 polynucleotide kinase, T4 RNA ligase and calf intestinal alkaline phosphatase from New England Biolabs.

Preparation of DNA and RNA

The RNAs used for this study were transcribed from DNA templates containing a T7 promotor (Milligan, J. F. et al. (1989) *Methods Enzymol.* 180, 51–62), DNA templates were generated by PCR amplification of synthetic oligonucleotides. PCR reactions were performed in PCR-buffer (10 mM Tris-HCl pH 8.3, 50 mM KCl, 0.001% gelatine, 1.5 mM $MgCl_2$, 0.3% Tween 20, 0.2 mM dNTPs) in the presence of 3 μM primer and 2U Taq Polymerase. Primers and synthetic oligonucleotides used in PCR amplification reactions were synthesized on a Millipore Expedite oligonucleotide synthesizer using standard phosphoramidite chemistry. For 5'-endlabeling, the transcribed RNA was dissolved in CIP buffer (50 mM Tris pH 8.5, 0.1 mM EDTA, 0.1 mg/ml BSA) and treated with 0.05 U of calf intestinal alkaline phosphatase per pmol RNA for 30 min at 37° C. After purification by preparative gel electrophoresis on polyacrylamide-8.3M urea gels, about 10 pmols of the eluted RNA were redissolved in kinase buffer (70 mM Tris-HCl pH 7.6, 10 mM $MgCl_2$, 5 mM DTT), 5'-endlabeled using 10 UT4 polynucleotide kinase and 30 μCi [γ-$^{32}$P]ATP for 30 min at 37° C. and again purified on polyacrylamide-8.3M urea gels.

For 3'-labeling, 30 pmols of RNA were incubated with 30 μci[5'-$^{32}$P]pCp in 50 mM Hepes pH 7.5 and 20 mM MgCl$_2$ in the presence of 6 U of T4 RNA ligase at 4° C. for 12–16 h followed by gel purification.

Flavin Cleavage Experiments 250 nM 5'-$^{32}$P-endlabeled RNA (approximately 10,000 cpm) was denatured in 200 mM NaCl, 50 mM Tris-HCl pH 7.6 and 2 mM EDTA for 3 min at 95° C. and subsequently renatured for 10 min at room temperature. After adding MgCl$_2$ to a final concentration of 12 mM, the RNA was irridated in the presence of 200 μM FMN or riboflavin at 25° C. for times up to 4 h using an incident light from a polychromatic lamp. The reaction was stopped by precipitation. The RNA was redissolved in H$_2$O and analyzed on polyacrylamide-8.3M urea gels. For calibration of gel band positions, 5'-labeled RNA was cleaved at G residues by digestion with T1 ribonuclease or was subjected to alkaline hydrolysis, respectively, as described by Donis-Keller, H. et al. (1977) *Nucl. Acids Res.* 4, 2527–38. For hydroxyl radical cleavage, the RNA was incubated in 1 mM Fe(NH$_4$)$_2$(SO$_4$)$_2$.6H$_2$O, 2 mM EDTA, 0.05% H$_2$O$_2$ and 5 mM DTT at 25° C. for 10 min. Hüttenhofer, A. et al. (1994) *EMBO J.* 13, 3892–901. Hüttenhofer, A. et al. (1992) *Proc. Natl. Acad. Sci. USA* 89, 7851–55.

EXAMPLE 1

Figure 2A:
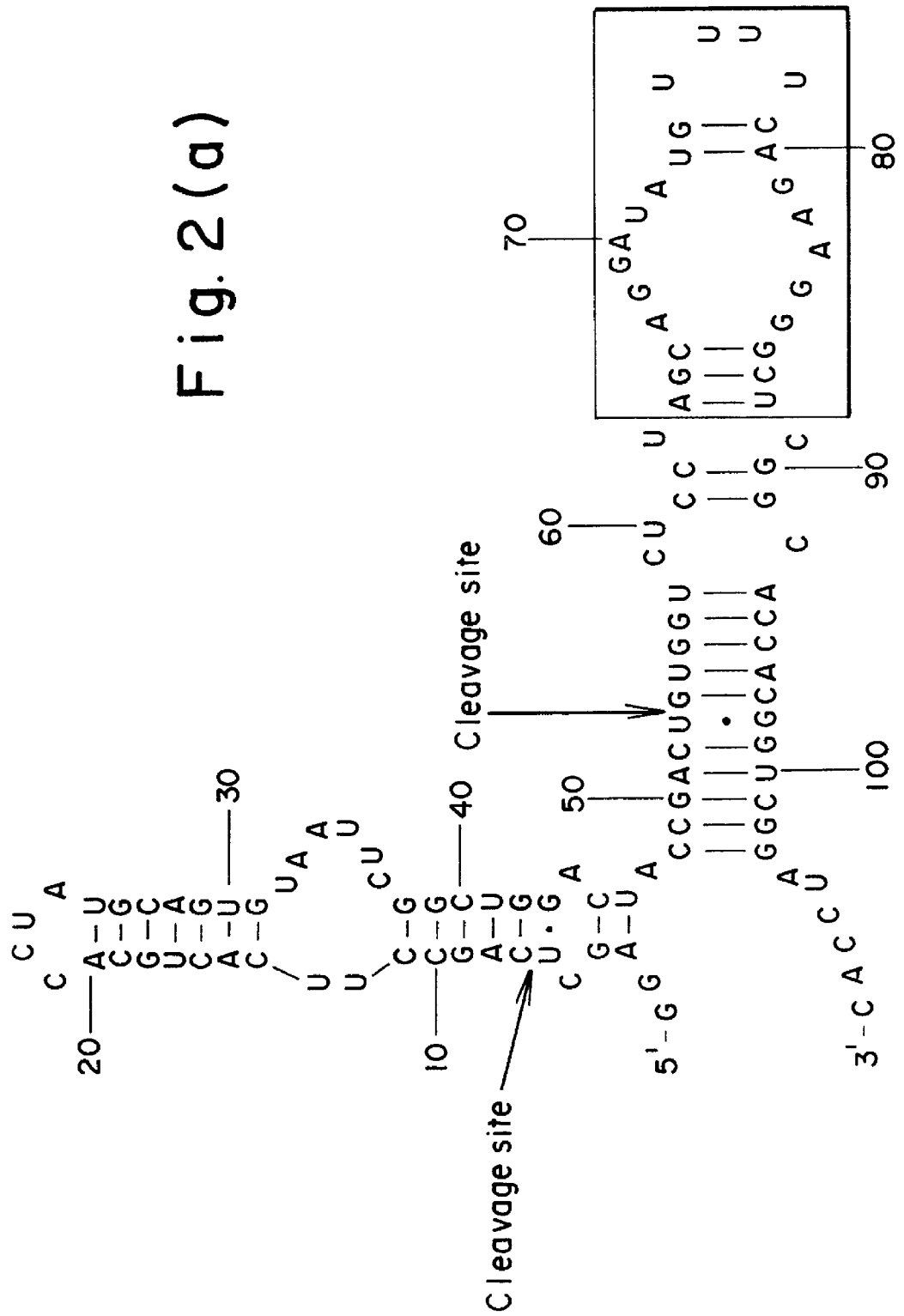
FIG. 2(a) shows the secondary structure of RNA FMN-2. The flavin binding site is highlighted. The sites of cleavage induced by FMN and irradiation are indicated by arrows.
Figure 2B:
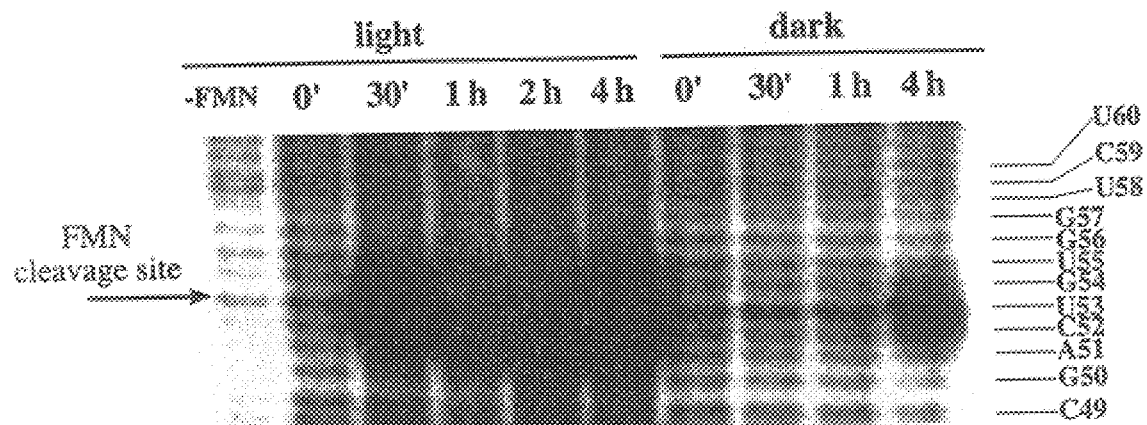
FIG. 2(b) shows the time dependence of the cleavage upon irradiation with light and in the dark. The cleavage site 3' of U53 is indicated by arrow.
Figure 2C:
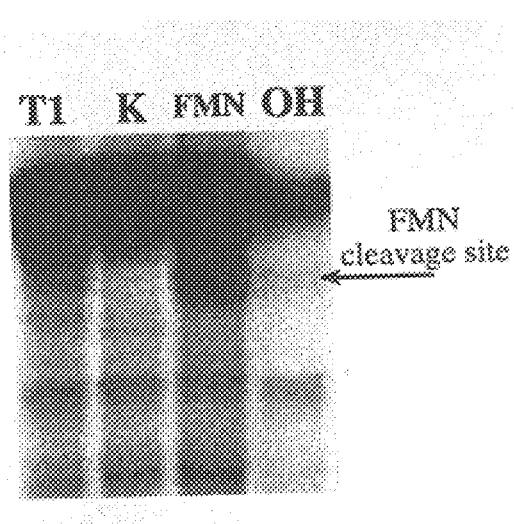
FIG. 2(c) shows the photoinduced cleavage of 3'-$^{32}$P-endlabeled RNA FMN-2. The arrow indicates the cleavage site at C7.

Referring to FIG. 2, incubation of the 5'-$^{32}$P-endlabeled RNA FMN-2 (the structure of which is shown in FIG. 2(*a*)) with 200 μM FMN in cleavage buffer (250 mM NaCl, 50 mM Tris-Cl, pH 7.6, 12 mM MgCl$_2$, 2 mM EDTA) leads to a cleavage product of 53 nt in length, as shown in FIG. 2(*b*). The cleavage occurs downstream of U53 which is part of a G-U wobble base pair within an 11-base pair helical region. The constitution of this stem and the G-U base pair was proven by chemical modification analyses (data not shown). In the secondary structure, a second G-U wobble base pair is formed by G43 and U6. Cleavage of the 5'-endlabeled RNA at this position could not be resolved in the gel (FIG. 2(*b*)). To test whether cleavage also occurs 3' of U6 we incubated the 3'-endlabeled RNA FMN-2 with FMN. Two cleavage products were obtained, one corresponding to cleavage 3' of U53 and another corresponding to cleavage 3' of U6 (FIG. 2 (*c*)). The strand breakage reaction proceeds in a time-dependent manner. Furthermore, cleavage can only be detected upon irradiation with visible light whereas no product is formed in the dark even at an incubation time of four hours (FIG. 2(*b*)).

EXAMPLE 2

Figure 3A:
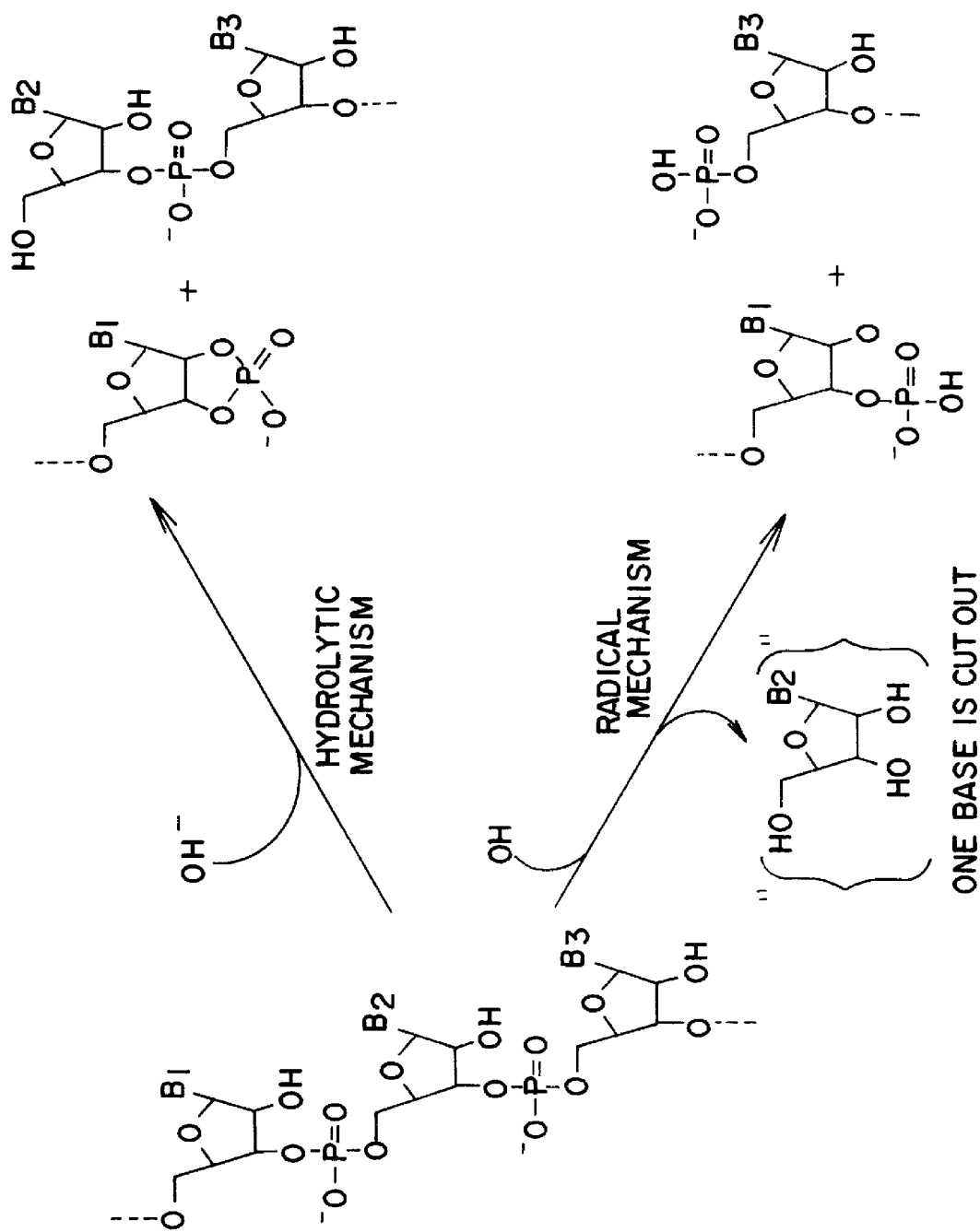
FIG. 3(a) shows the mechanisms of hydrolytic and oxidative cleavage reactions of RNA.
Figure 3B:
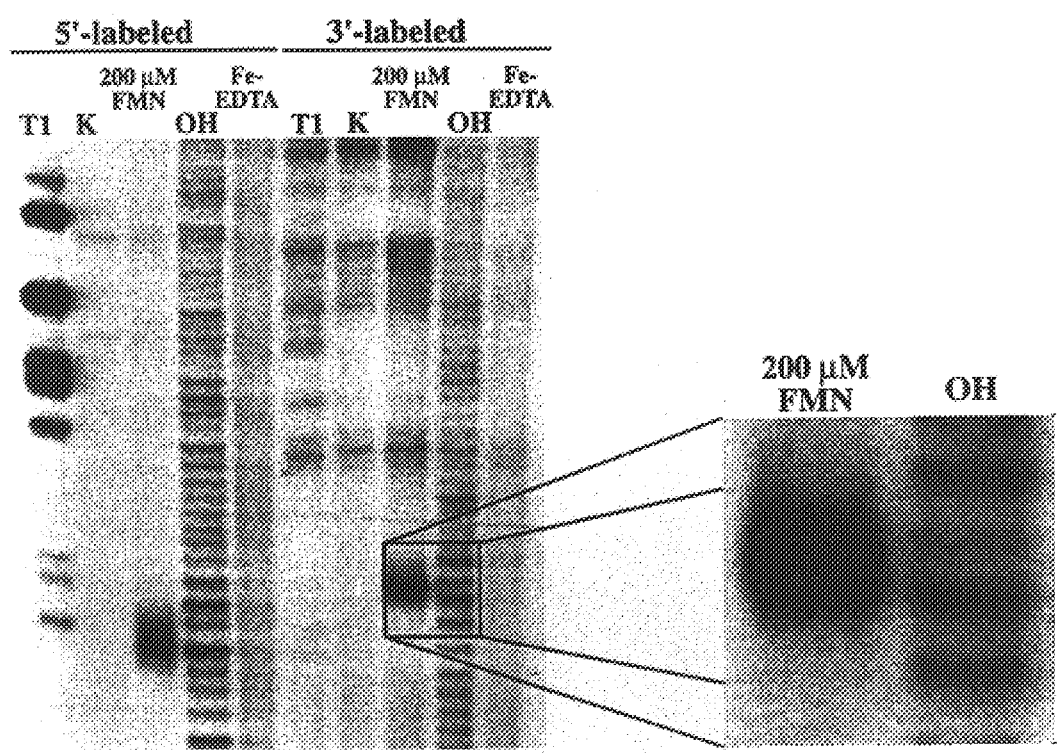
FIG. 3(b) shows the cleavage of 5'- and 3'-$^{32}$P-endlabeled RNA FMN-2 with 200 μM FMN and visible light for 1 h at 25° C.

To analyze the end groups formed in the cleavage reaction, the migration of the cleaved RNA was compared with the products obtained in a hydrolytic and oxidative cleavage reaction (FIG. 3). In a hydrolytic mechanism, the 2'-hydroxyl group of the nucleoside which is located 5' to the cleaved phosphodiester bond carries out a nucleophilic attack on the phosphorus atom. This attack results in strand breakage and the formation of 5'-hydroxyl and 2',3'-cyclic phosphate ends at the cleavage site. In oxidative cleavage processes, the ribose ring is destroyed, leading to the loss of one nucleotide and the generation of 5'phosphate and 3'-phosphate or phosphoro glycolate termini. This process is shown in FIG. 3(*a*). The 3'-endlabeled substrate used in this process permitted analysis of the 5'-termini created at the cleavage site (FIG. 3(*b*)). The product of the FMN cleavage migrated between the bands of the alkaline hydrolysis ladder, but exactly at the same position as the bands generated by Fe-EDTA cleavage demonstrating the formation of a 5'-phosphate terminus, in accordance with an oxidative cleavage mechanism. Thus, this experiment shows that the termini generated during the cleavage of RNA by FMN are the same as the ends produced in oxidative cleavage mechanisms.

Comparison of the position of the cleavage bands for the 5'- and 3'-labeled substrates relative to the RNase T1 sequencing lanes (FIG. 3(*b*)) shows that the 5'-labeled product terminates at residue U53 whereas the 3'-labeled product ends at U55. This observation is consistent with the notion that the residue 3' to the uracil of the G-U base pair, G54, is cut out during the cleavage process. This result is also in agreement with the chemistry of oxidative cleavage processes.

EXAMPLE 3

For further characterization of the cleavage reaction, experiments with different flavin derivatives were carried out. The results of these experiments are presented in FIG. 4. Riboflavin, which lacks the phosphate group of FMN, and lumiflavin show the same cleavage products and the same activity as FMN. In contrast, FAD and lumichrome are inactive in the cleavage reaction. These results confirm that the induced strand breakage is based on a photosensitizer reaction, because FAD is known to be non-photosensitizing. Lumichrome cannot be expected to perform an oxidative cleavage reaction since the different conjugation in the alloxazine ring system does not permit the required reduction of the molecule in the cleavage mechanism, in contrast to the isoalloxazine moiety.

EXAMPLE 4

Figure 5:
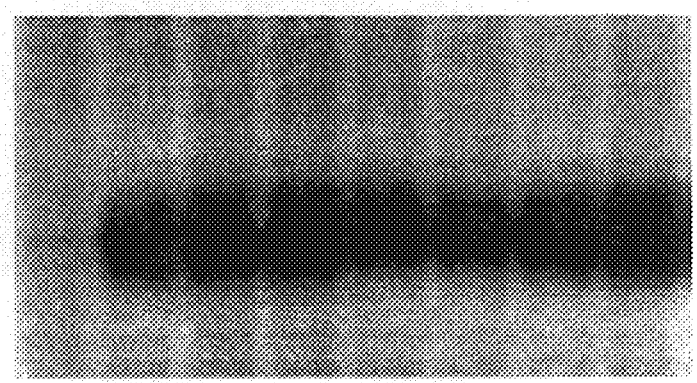
FIG. 5 shows the effect of $MgCl_2$ on the photoinduced cleavage of 5'-$^{32}$P-endlabeled RNA FMN-2 with 200 μM FMN, carried out for 1 h at 25° C.

Because divalent metal ions, especially magnesium, are important for maintaining the secondary and tertiary structure of RNA, the dependence of the cleavage reaction on $Mg^{2+}$ and other divalent metal ions was analysed. As presented in FIG. 5, no cleavage was observed without any divalent cation, whereas an efficient concentration of 1 mM MgCl$_2$ was sufficient for cleavage. All cleavage reactions contained 2.0 mM EDTA and were supplemented with the bivalent metal ion to be tested. No increase in the amount of cleavage product in the presence of $Mg^{2+}$ concentrations above 1.0 mM was observed. 4 h of incubation with $Mg^{2+}$-free buffer resulted in negligible amounts of cleavage product (data not shown). Table 1 summarizes the activity of cleavage obtained when magnesium ions were substituted for other divalent cations such as $Ca^{2+}$, $Sr^{2+}$, $Ba^{2+}$, $ZN^{2+}$, and $Cd^{2+}$. The latter resulted in the same strand cleavage pattern, whereas $Mn^{2+}$, $Cu^{2+}$, or $Pb^{2+}$ were not able to substitute for the aforementioned ions.

TABLE 1

|  | $Mg^{2+}$ | $Ca^{2+}$ | $Sr^{2+}$ | $Ba^{2+}$ | $Zn^{2+}$ | $Cd^{2+}$ | $Mn^{2+}$ | $Cu^{2+}$ | $Pb^{2+}$ |
|---|---|---|---|---|---|---|---|---|---|
| mediates cleavage | + | + | + | + | + | + | − | − | − |

Tests were performed to discover whether the cleavage mechanism depends on the sodium concentration (results not shown). It was found that cleavage takes place in sodium-free cleavage buffer. Therefore, monovalent cations appear not to be required for the cleavage reaction.

EXAMPLE 5

To exclude the possibility that the flavin-dependent cleavage was characteristic for the particular FMN-binding RNA FMN-2, at which the cleavage phenomenon was first observed, five different FMN binding aptamers were incubated with 200 $\mu$M FMN. The results of these experiments are shown in Table 2. The secondary structure models were generated by computer foldings using the Zuker algorithm. Zucker, M. et al. (1991) *Nucl. Acids Res.* 19, 2707–14. Among 14 G-U base pairs proposed for the six RNAs, 10 showed the expected cleavage pattern. As with the FMN-2 RNA, cleavage occurred downstream of the uracil participating in the base pairing regardless of the nature of the nucleotide located 3' of the uracil. This result demonstrates that FMN-induced RNA cleavage is not restricted to the FMN-2 RNA.

TABLE 2

| RNA | cleavage at | no cleavage at | residue 3' of U |
|---|---|---|---|
| FMN-2 | | | |
| FMN-5 | G1-U51 | | A |
| | G2-U50 | | U |
| | G18-U33 | | A |
| | G103-U60 | | G |
| FMN-7 | G2-U51 | | C |
| | G18-U33 | | U |
| | | G22-U29 | G |
| FMN-9 | G24-U58 | | G |
| | G63-U20 | | C |
| | | G29-U44 | C |
| FMN-13 | G9-U68 | | U |
| | G18-U52 | | U |
| | G49-U21 | | U |
| | | G28-U38 | A |
| FMN-24 | | G64-U17 | G |
| tRNA$^{Phe}$ | | | |
| tRNA$^{ASP}$ | | | |
| tRNA$^{fMet}$ | | | |
| td-intron | | | |

EXAMPLE 6

Figure 6A:
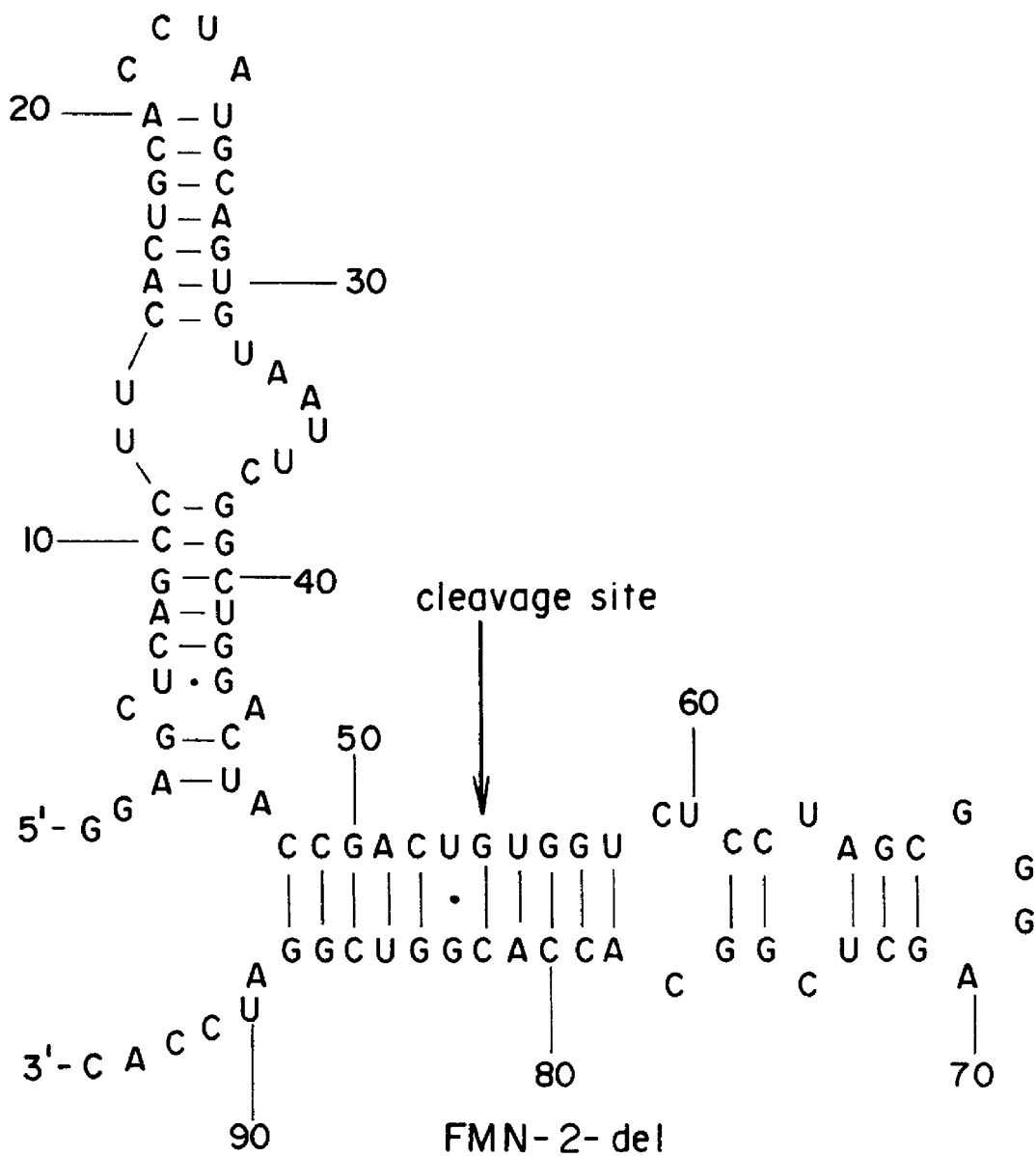

To investigate whether the flavin-induced RNA cleavage requires the specific FMN binding site contained in the RNA aptamers used, a truncated RNA version of the aptamer FMN-2 in which the complete flavine binding site was deleted was tested in the cleavage reaction (FIG. 6). This construct still contains the 11-base pair stem in which the cleaved G-U base pair is located. The RNA FMN-2.del (FIG. 6(a)) had completely lost its affinity for FMN, as confirmed by a binding assay using FMN agarose (data not shown).

Figure 6B:
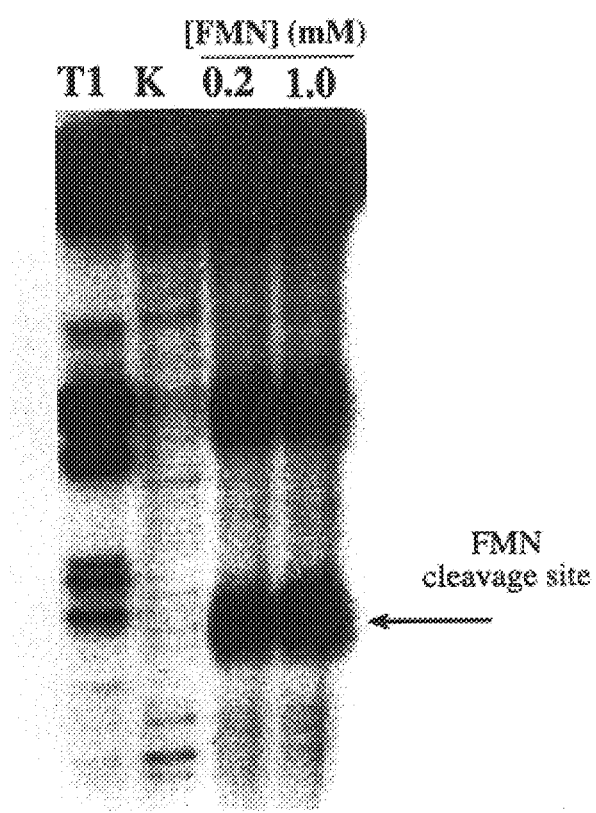
FIG. 6(b) shows the effect of RNA FMN-2.del, incubated for 1 h at 25° C.

The formation of the 11-base pair stem was also confirmed by chemical modification analyses. FIG. 6(b) demonstrates that FMN-2.del was cleaved at exactly the same site as FMN-2. This result clearly shows that the cleavage reaction does not require the FMN recognition site contained in the aptamers.

EXAMPLE 7

It was asked next whether this cleavage mechanism could be applied to biologically relevant RNAs (FIG. 7). RNAs with a known secondary and tertiary structure and without any affinity for flavins were chosen to demonstrate that the photoinduced cleavage of RNA by flavin derivatives is a general mechanism. Representatives of RNAs which fulfill these criteria are, for example, the tRNA$^{Phe}$ or tRNA$^{Asp}$ from yeast because of their published crystal structures. Yeast tRNA$^{Phe}$ contains a single G-U wobble base pair formed by G4 and U69. The results of the irradiation of tRNA$^{Phe}$ incubated with 200 $\mu$M FMN for 1 h in the presence of light is presented in FIG. 7(a). A single cleavage site corresponding to the excision of C70 was observed (see arrow).

The corresponding results for yeast tRNA$^{Asp}$ are presented in FIG. 7(b). tRNA$^{Asp}$ contains three G-U base pairs (G68-U5, G10-U25, G30-U40) and one G22-$\Psi$13 base pair. A major cleavage signal was obtained for G68-U5, a less intensive band was observed at G30-U40. This band also migrates between the bands of the alkaline hydrolysis ladder, which confirms the cleavage mechanism concluded from FIG. 3. No cleavage was detected at the G10-U25 and the G-$\Psi$ base pairs, both of which flank the D-stem.

tRNA$^{fMet}$ from yeast also contains a single G-U pair in the T-stem. This base pair is also recognized and cleaved by FMN, as shown in FIG. 7(c). No other position within this tRNA is affected by the photosensitizer.

EXAMPLE 8

Referring to FIG. 8, as a fourth model system, we incubated the precursor RNA of the T4 phage derived thymidilate synthase (td) intron with FMN (FIG. 8). The 265 nt group I intron contains several G-U base pairs located within stems or as closing base pairs of loops as shown in the secondary structure model in FIG. 8.

Referring again to FIG. 8, the gel analyzing the 5'-labeled intron reveals a major site of cleavage 3' of U102 which forms a base pair with G90 and two minor cleavage sites downstream of U72-G53 and U93-G99. Two other strong bands are visible in the region close to the 3'-end which could not be assigned to a particular position because of poor resolution of the gel in this region, but presumably correspond to U152 and U253, respectively. To resolve observed bands located near the 3'-end of the RNA the 3'-labeled intron was analyzed. This analysis confirmed that these two additional cleavages occur at the two G-U pairs located in stems P7.2 and P9.2. No cleavage could be detected in stem P1 which contains two consecutive G-U base pairs and at G232 and U219 in stem P9.1. The observed cleavage sites are represented in the three dimensional model of the td-intron (Westhof, unpublished data).

We claim:

1. A method of cleaving an RNA molecule containing at least one G-U wobble base pair at the at least one G-U wobble base pair thereof, comprising:

combining the RNA molecule with (a) a photosensitizing flavin derivative which is capable of performing a photooxidative reaction with the RNA molecule upon irradiation with light and (b) a divalent metal cation, or salt thereof, to produce a mixture; and thereafter removing one nucleotide downstream of the U of the at least one G-U wobble base pair to cleave the RNA molecule immediately downstream of the U of the at least one G-U wobble base pair thereof by irradiating the mixture with light.

2. The method of claim 1, wherein the mixture is irradiated for an exposure time of 45 to 60 minutes.

3. The method of claim 1, wherein the divalent metal cation or salt thereof is present in a concentration of 2 to 50 mM.

4. The method of claim 1, wherein the photosensitizing flavin derivative is present in a concentration of 20 to 300 µM.

5. The method of claim 1, wherein the RNA molecule is selected from the group consisting of tRNA$^{Phe}$ and tRNA$^{Asp}$.

6. The method of claim 1, wherein the RNA molecule is devoid of a flavin-binding region.

7. The method of claim 1, wherein the photosensitizing flavin derivative is selected from the group consisting of flavin mononucleotide, lumiflavin and riboflavin.

8. The method of claim 1, wherein the divalent metal cation is selected from the group consisting of $Mg^{2+}$, $Ca^{2+}$, $Sr^{2+}$, $Ba^{2+}$, $Zn^{2+}$ and $Cd^{2+}$.

9. The method of claim 1, wherein the light is visible light.

10. A method of detecting a G-U wobble base pair in an RNA molecule, comprising:

combining the RNA molecule with (a) a photosensitizing flavin derivative which is capable of performing a photooxidative reaction with the RNA molecule upon irradiation with light and (b) a divalent metal cation, or salt thereof, to produce a mixture;

thereafter irradiating the mixture with light to cleave the RNA molecule immediately downstream of the U of the G-U wobble base pair thereof, to produce at least one cleavage product; and detecting the at least one cleavage product.

11. The method of claim 10, wherein the mixture is irradiated for an exposure time of 45 to 60 minutes.

12. The method of claim 10, wherein the divalent metal cation or salt thereof is present in a concentration of 2 to 50 mM.

13. The method of claim 10, wherein the photosensitizing flavin derivative is present in a concentration of 20 to 300 µM.

14. The method of claim 10, wherein the RNA molecule is devoid of a flavin-binding region.

15. The method of claim 10, wherein the photosensitizing flavin derivative is selected from the group consisting of flavin mononucleotide, lumiflavin and riboflavin.

16. The method of claim 10, wherein the divalent metal cation is selected from the group consisting of $Mg^{2+}$, $Ca^{2+}$, $Sr^{2+}$, $Ba^{2+}$, $Zn^{2+}$ and $Cd^{2+}$.

17. The method of claim 10, wherein the light is visible light.

* * * * *